(12) United States Patent
Kwon et al.

(10) Patent No.: US 7,396,457 B2
(45) Date of Patent: Jul. 8, 2008

(54) APPARATUS AND METHOD FOR RECOVERING ACETIC ACID AND CATALYST IN PROCESS FOR PREPARATION OF 2,6-NAPHTHALENEDICARBOXYLIC ACID

(75) Inventors: Ik-Hyun Kwon, Kyonggi-do (KR); Young-Gyo Choi, Kyonggi-do (KR); Byung-Jun Song, Kyonggi-do (KR); Jong-Cheul Ji, Kyonggi-do (KR)

(73) Assignee: Hyosung Corporation, Kyonggi-do (KR)

(*) Notice: Subject to any disclaimer, the term of this patent is extended or adjusted under 35 U.S.C. 154(b) by 0 days.

(21) Appl. No.: 11/475,099

(22) Filed: Jun. 27, 2006

(65) Prior Publication Data

US 2007/0299235 A1  Dec. 27, 2007

(51) Int. Cl.
*B01D 9/00* (2006.01)
*B01D 69/10* (2006.01)
*C07C 7/14* (2006.01)

(52) U.S. Cl. .................. 210/178; 210/179; 210/180; 210/321.6

(58) Field of Classification Search ................ 210/175, 210/178, 179, 252, 259, 321.6, 180
See application file for complete search history.

(56) References Cited

U.S. PATENT DOCUMENTS

| | | | |
|---|---|---|---|
| 1,754,599 A * | 4/1930 | Bollmann ................. 554/191 |
| 1,818,452 A * | 8/1931 | Baylis ..................... 554/191 |
| 2,199,670 A * | 5/1940 | Lowry ..................... 210/179 |
| 2,579,637 A * | 12/1951 | Weltman et al. ......... 427/389.9 |
| 3,880,920 A | 4/1975 | Wampfler |
| 4,353,784 A | 10/1982 | Koga et al. |
| 4,515,684 A * | 5/1985 | Brown ..................... 208/180 |
| 4,794,195 A * | 12/1988 | Hayashi et al. ........... 562/414 |
| 4,883,912 A | 11/1989 | Koga et al. |
| 4,939,297 A | 7/1990 | Browder et al. |
| 5,009,789 A * | 4/1991 | Helmer et al. ............ 210/641 |
| 5,132,450 A | 7/1992 | Tanaka et al. |
| 2002/0016500 A1 | 2/2002 | Matsumoto et al. |
| 2004/0237859 A1* | 12/2004 | Hartmann ................. 110/341 |
| 2004/0244536 A1 | 12/2004 | Lin |
| 2004/0245176 A1 | 12/2004 | Parker et al. |

FOREIGN PATENT DOCUMENTS

| | | |
|---|---|---|
| EP | 0 181 127 A2 | 5/1986 |
| EP | 0 465 100 A1 | 1/1992 |
| EP | 1 167 336 A2 | 1/2002 |
| EP | 1 484 307 A | 12/2004 |
| JP | 10-304899 | * 11/1998 |
| WO | WO 01/12318 A | 2/2001 |

OTHER PUBLICATIONS

Global Spec; Mar. 25, 2005; XP002405331; http://separationequipment.globalspec.com/LearnMore/Processing_Equipment/Filtration_Separation_Products/Liquid_Solid_Filtration_Separation_Equipment.

* cited by examiner

*Primary Examiner*—Fred Prince
(74) *Attorney, Agent, or Firm*—Nixon & Vanderhye P.C.

(57) ABSTRACT

An apparatus and a method for effectively recovering acetic acid and catalyst from a mother liquor discharged from a series of processes including an oxidation process, a crystallization process and a solid-liquid separation process, in a continuous process for preparing naphthalenedicarboxylic acid by oxidizing dimethylnaphthalene in the presence of an oxygen-containing gas and an acetic acid solvent, using a catalyst system comprising a transition metal such as cobalt or manganese, and a bromine-based compound, are provided.

4 Claims, 1 Drawing Sheet

APPARATUS AND METHOD FOR RECOVERING ACETIC ACID AND CATALYST IN PROCESS FOR PREPARATION OF 2,6-NAPHTHALENEDICARBOXYLIC ACID

BACKGROUND OF THE INVENTION

1. Field of the Invention

The present invention relates to an apparatus and a method for effectively recovering acetic acid and catalyst from a mother liquor discharged from a series of processes including an oxidation process, a crystallization process and a solid-liquid separation process, in a continuous process for preparing naphthalenedicarboxylic acid by oxidizing dimethyl-naphthalene in the presence of an oxygen-containing gas and an acetic acid solvent, using a catalyst system comprising a transition metal such as cobalt or manganese, and a bromine-based compound.

2. Description of the Related Art

In general, a variety of separation processes can be employed to recover acetic acid and catalyst that have been used in the process.

For the method of recovering acetic acid, it is common to use an acetic acid recovery process using a distillation method, but this process is economically unfavorable. Meanwhile, a filtration method and an absorption method are not suitable for separating acetic acid and catalyst. Thus, a variety of different methods for recovering acetic acid and catalyst have been suggested. U.S. Pat. No. 4,883,912 describes a process for recovering acetic acid by extracting acetic acid from an acetic acid solution containing metallic substances, using tertiary amine and an organic diluent as the solvent for acetic acid extraction. However, this method is not suitable as the method for recovering acetic acid and catalyst in the process for preparation of naphthalenedicarboxylic acid, because the method of extraction requires a post-treatment process after the separation and recovery of acetic acid, and the reactivities of the solvent for extraction and of the oxidation catalyst need to be taken into account.

There are available an incineration method, a vacuum filtration method, and an electrochemical method as the methods for catalyst recovery, but these methods are still not commercialized.

SUMMARY OF THE INVENTION

Accordingly, it is an object of the present invention to solve the aforementioned technical problems and disadvantages of the prior art and therefore, to provide an apparatus and a method for economically and efficiently recovering acetic acid and catalyst from a mother liquor discharged from the process for preparation of naphthalenedicarboxylic acid.

DESCRIPTION OF THE PREFERRED EMBODIMENTS

Figure 1:
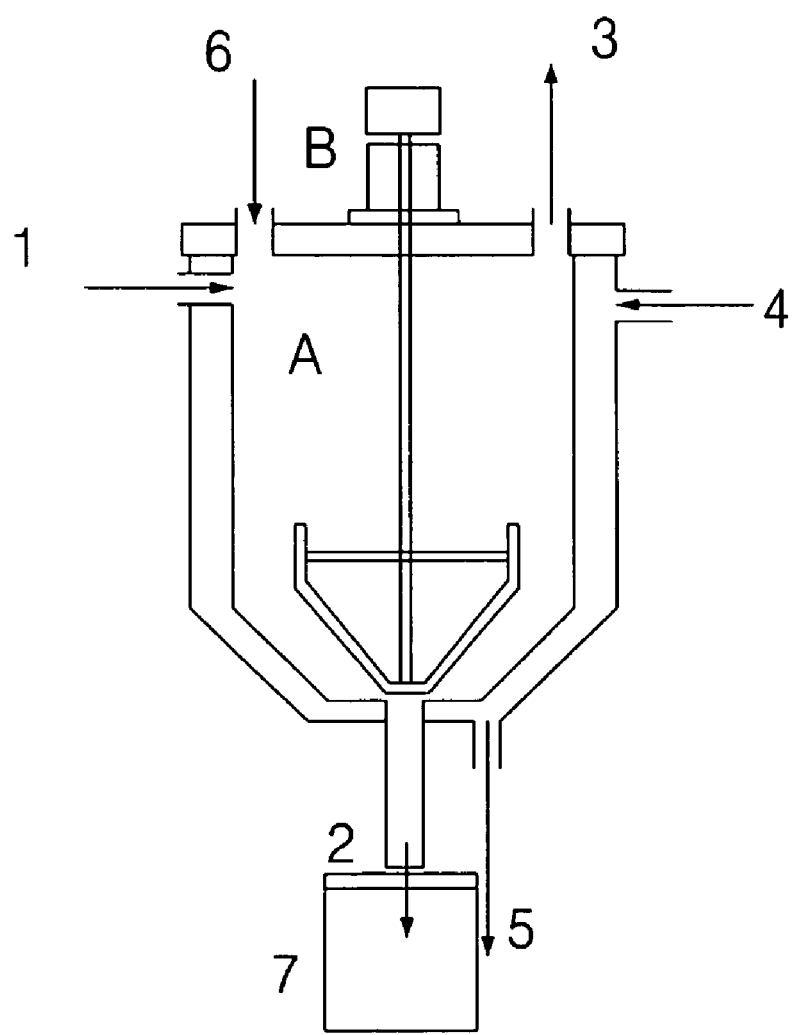
FIG. 1 is a schematic diagram illustrating an apparatus for recovering acetic acid and catalyst from a mother liquor discharged from the process for preparation of 2,6-naphthalenedicarboxylic acid according to an embodiment of the present invention.

In order to achieve the above-described object, the present invention provides an apparatus and a method for recovering acetic acid and catalyst from a mother liquor discharged from the process for preparation of naphthalenedicarboxylic acid.

According to an embodiment of the invention, there is provided an apparatus for recovering acetic acid and catalyst from a mother liquor discharged from the process for preparation of naphthalenedicarboxylic acid, containing acetic acid, catalyst and other organic materials, which comprises a mother liquor receptacle including an inlet for introducing the mother liquor or sodium hydroxide, an outlet for acetic acid, and an outlet for catalyst and organic materials; a heating means for heating the mother liquor receptacle; a downstream membrane filter connected to the outlet for catalyst and organic materials for separating the catalyst from the organic materials; and an agitator for agitating the inside of the mother liquor receptacle.

According to other embodiment of the invention, the heating means is a jacket including an inlet for steam attached around the external wall of the mother liquor receptacle and an outlet for condensed water.

According to another embodiment of the invention, the mother liquor receptacle may further include an inlet for sodium hydroxide.

According to still another embodiment of the invention, the apparatus for recovering acetic acid and catalyst has a shape of cone or truncated cone.

According to still another embodiment of the invention, the downstream membrane filter has a degree of vacuum of 50 to 150 mmHg, a total filter area of 0.3 to 0.7 m$^2$, and a membrane pore size of 20 to 80 µm.

According to still another embodiment of the invention, there is provided a method for recovering acetic acid and catalyst from a mother liquor discharged after the process for separation of naphthalenedicarboxylic acid, which comprises the steps of receiving the mother liquor discharged after the process for separation of naphthalenedicarboxylic acid; recovering acetic acid in a gaseous state by heating the received mother liquor; and separating and recovering the catalyst by introducing sodium hydroxide to the residue remaining after the recovery of acetic acid to precipitate the catalyst.

According to still another embodiment of the invention, sodium hydroxide may be introduced in an amount of 2- to 3-folds of the percentage by weight of the remaining acetic acid.

According to still another embodiment of the invention, a vacuum filtration method is used for the recovery of catalyst.

According to still another embodiment of the invention, the method of the invention is carried out in a totally integrated process using the apparatus described above. Here, the term totally integrated process implies that a series of processes for recovering acetic acid and catalyst are carried out not in the separate apparatuses, but in a single apparatus.

Hereinafter, the invention will be described in detail with reference to FIG. 1, which is a schematic diagram of an embodiment of the invention.

The upper part of the mother liquor receptacle A is equipped with an inlet for mother liquor 1, which receives the mother liquor discharged from the process for preparation of naphthalenedicarboxylic acid. The received mother liquor is heated by the external heating means, and at this time, acetic acid vaporizes and is discharged through the outlet for acetic acid 3. The residue remaining after the discharge of acetic acid comprises catalyst and other organic materials, and sodium hydroxide is introduced to the residue to precipitate the catalyst. The introduction of sodium hydroxide can be achieved through a separate inlet 6, but can be also achieved through the inlet for mother liquor 1. The precipitated catalyst is discharged through an outlet 2 for catalyst and organic materials, and then is separated from the organic materials through the downstream membrane filter 7 to be finally recovered. mother liquor is heated by the external heating means, and at this time, acetic acid vaporizes and is discharged through the outlet for acetic acid 3. The residue remaining after the discharge of acetic acid comprises catalyst and other organic materials, and sodium hydroxide is introduced to the residue to precipitate the catalyst. The introduction of sodium hydroxide can be achieved through a separate inlet 6, but can be also achieved through the inlet for mother liquor 1. The precipitated catalyst is discharged through an outlet for catalyst and organic materials, and then is separated from the organic materials through the downstream membrane filter 7 to be finally recovered.

The mother liquor receptacle is equipped with an agitator B for agitating the mother liquor, the catalyst-containing residue, or the like, and the agitator is preferably an anchor type agitator.

For the mother liquor heating means, for example, steam at 170 to 190° C. is introduced to the inlet for steam 4, which serves as an inlet for heat supplying medium, to heat the mother liquor in the mother liquor receptacle. The introduced steam is condensed and discharged through the outlet for downstream condensed water 5.

For the catalyst used for oxidizing dimethylnaphthalene to naphthalenedicarboxylic acid, a complex catalyst system comprising a combination of a cobalt component, a manganese component and a bromine component is used. The compound that can be used as the cobalt component in the complex catalyst system may be exemplified by cobalt acetate, cobalt naphthalate, cobalt carbonate or the like, and the amount of the cobalt component, expressed as the ratio of cobalt atoms to dimethylnaphthalene, is 0.02 to 0.15, preferably 0.04 to 0.12, and more preferably 0.06 to 0.1.

The compound that can be used as the manganese component may be exemplified by manganese acetate, manganese naphthalate, manganese carbonate or manganese bromide, and the amount of the manganese component, expressed as the ratio of manganese atoms to cobalt atoms, is 0.05 to 1.0, and preferably 0.15 to 0.4. The total amount of metal catalyst, that is, the sum of the cobalt component and manganese component, expressed as the ratio of metal atoms to dimethylnaphthalene, is 0.03 to 0.25, and preferably 0.05 to 0.2. When these amounts exceed the given ranges, the desired high purity naphthalenedicarboxylic acid cannot be obtained. When the cobalt component and the manganese component are used in excessively small amounts, conversion of 2,6-formylnaphthoic acid which is an intermediate compound of the oxidation reaction does not occur, and the yield for the final target product is reduced. When these components are used in excessively large amounts, the metal components will form complexes with trimellitic acid, which is an impurity, thus lowering the purity of naphthalenedicarboxylic acid.

The compound that can be used to supply the bromine component may be exemplified by at least one compound selected from the group consisting of manganese bromide, cobalt bromide, sodium bromide, ammonium bromide and tetrabromoethane, and the amount of the bromine component, expressed as the ratio of the bromine component to cobalt atoms, is 0.8 to 2.0, and preferably 1.0 to 1.5. When the bromine component is used in an amount exceeding the given range, the amount of the transition metal complex of naphthalenedicarboxylic acid that is finally induced is reduced, but the amount of the bromine compounds increases, and subsequently, the purification process will be overloaded, with an undesirable increase in the amount of colored impurities produced. Furthermore, when a process of reusing the bromine component is to be employed, the necessity for a recovery process leads to additional economic loss. On the other hand, when the bromine component is used in an amount less than the given range, the amount of transition metal complex in the final product of naphthalenedicarboxylic acid will increase.

The reactant dimethylnaphthalene is dissolved in acetic acid at a ratio of 1:5 to 1:15, and preferably at a ratio of 1:10 to 1:12, and is introduced to the oxidizing reactor.

The obtained product after the oxidation process become to a slurry state comprising a solid-phase component of a constant size and the acetic acid through a crystallization process, the slurry is transported to a solid-liquid separation process. Then, the slurry is separated into the solid-phase component of product and mother liquor, that is, the acetic acid solution containing the catalyst and organic materials, by the apparatus used for the separation process. The invention is characterized in that acetic acid and catalyst contained in the mother liquor discharged from the solid-liquid separation process are effectively separated.

In the apparatus for recovering acetic acid and catalyst according to the invention, acetic acid is recovered by introducing steam which is a heat supplying medium, to vaporize acetic acid, while the catalyst in the remaining solution not evaporated is recovered by introducing sodium hydroxide to precipitate the catalyst, and then vacuum filtering the catalyst precipitate.

The apparatus for recovering acetic acid and catalyst according to the invention is characterized in that a jacket is provided around the external wall of the apparatus in order to use a heat supplying medium as the mother liquor-heating means intended for the evaporation of acetic acid.

It is preferable to introduce sodium hydroxide in an amount of 2- to 3-folds of the percentage by weight of the remaining acetic acid, so that the amount of sodium hydroxide is sufficient to neutralize the remaining acetic acid and other organic materials.

The membrane filter used for vacuum filtration has a total filter area of 0.3 to 0.7 $m^2$, and a pore size of 20 to 80 μm, and the degree of vacuum is maintained at 50 to 150 mmHg.

Hereinafter, the invention will be described in more detail with reference to Examples, but these Examples are not intended to limit the scope of the invention by any means.

EXAMPLE 1

A 300-L oxidizing reactor made of titanium, which was equipped with a cooler, a heater, an agitator and a recycling acetic acid drum, was charged with the catalyst and reactants as described in Table 1 below.

TABLE 1

| Material | Amount introduced |
|---|---|
| Cobalt | 6.21 wt % |
| Manganese | 1.58 wt % |
| Bromine | 3.87 wt % |
| Distilled water | 25.0 wt % |
| Acetic acid | Balance |

The reaction temperature and the reaction pressure were adjusted to 200° C. and 20 kg/$cm^2$, respectively. Then, the agitator was operated at 700 rpm to appropriately disperse the reactant gases introduced. A reaction solution containing 10% by weight of dimethylnaphthalene in acetic acid was supplied together with the catalyst to the oxidizing reactor at a rate of 93 kg/hr, and the reaction was carried out in a continuous mode.

After completion of the reaction, the mother liquor discharged after passing through the crystallization process and the separation process was introduced into the apparatus for acetic acid and catalyst recovery. The apparatus for acetic acid and catalyst recovery was made of stainless steel and had an internal volume of 107 L. The apparatus was equipped with a jacket around the external wall, in which a heat supplying medium was circulated, and an anchor type agitator was installed inside the apparatus. The heat supplying medium was steam at a pressure of 10 atmospheres, and was supplied until 70% or more of acetic acid evaporated. After the evaporation of acetic acid, 50 L of sodium hydroxide was introduced, while maintaining the temperature at 60° C. After about 2 hours, a filter and a vacuum pump were connected to the outlet for catalyst and organic materials, the organic materials and the reaction solution were filtered, and the remaining catalyst was recovered.

As a result, a recovery rate of 95% for the cobalt catalyst metal, a recovery rate of 90% for the manganese catalyst metal, a recovery rate of 10% for bromine, and a recovery rate of 65% for acetic acid are obtained.

It was confirmed from the results that the recovery of acetic acid and catalyst using the apparatus of the invention is economically advantageous.

The apparatus for recovering acetic acid and catalyst according to the invention is advantageous in that acetic acid and the catalyst can be conveniently recovered in a series of processes by using a single apparatus, not like conventional technologies. It is also possible to recover recyclable acetic acid and catalyst without any additional purification process, thus the process being economical.

What is claimed is:

1. An apparatus for recovering acetic acid together with catalyst from a mother liquor discharged from a process for preparation of 2,6naphthalenedicarboxylic a acid, containing acetic acid, catalyst and o the apparatus compnsing:
   a mother liquor receptacle having said mother liquor therein and including an inlet for receiving the mother liquor or sodium hydroxide, an outlet for acetic acid, and an outlet for catalyst and organic materials;
   a heating means for heating the mother liquor receptacle;
   an acetic acid outlet mounted on an upper part of the mother liquor receptacle for discharging acetic acid to be vaporized after the received mother liquor is heated by the heating means:
   a sodium hydroxide inlet to precipitate catalyst and organic materials from the residue remaining after the discharge of acetic acid;
   an outlet for catalyst and organic materials mounted on a lower part of the mother liquor receptacle for discharging the precipitated catalyst and organic materials;
   a downstream membrane filter connected to and mounted on a lower part of the outlet for catalyst and organic materials for separating the catalyst from the organic materials; and
   an agitator for agitating the inside of the mother liquor receptacle.

2. The apparatus of claim 1, wherein the heating means is a jacket including an inlet for steam attached around the external wall of the mother liquor receptacle, and an outlet for condensed water.

3. The apparatus of claim 1, wherein the apparatus has a shape of cone or truncated cone.

4. The apparatus of claim 1, wherein the downstream membrane filter has a degree of vacuum of 50 to 150 mmHg, a total filter area of 0.3 to 0.7 $m^2$, and membrane pore size of 20 to 80 μm.

* * * * *